US00PP33988P2

(12) United States Plant Patent
Losert

(10) Patent No.: US PP33,988 P2
(45) Date of Patent: Mar. 1, 2022

(54) ***CALIBRACHOA* PLANT NAMED 'KLECA20803'**

(50) Latin Name: ***Calibrachoa* sp.**
Varietal Denomination: KLECA20803

(71) Applicant: Klemm+Sohn GmbH & Co. KG, Stuttgart (DE)

(72) Inventor: Dominik Losert, Aspach (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 17/386,163

(22) Filed: Jul. 27, 2021

(51) Int. Cl.
*A01H 5/02* (2018.01)
*A01H 6/82* (2018.01)

(52) U.S. Cl.
USPC ..... Plt./413

(58) Field of Classification Search
USPC ..... Plt./413
CPC ... A01H 5/02; A01H 5/00; A01H 5/12; A01H 6/82; A01H 6/821
See application file for complete search history.

*Primary Examiner* — June Hwu
(74) *Attorney, Agent, or Firm* — Weatherly IP Solutions, LLC; Barbara Campbell

(57) ABSTRACT

A new *Calibrachoa* plant designated 'KLECA20803' particularly distinguished by a semi-trailing plant habit, and yellow flowers with red venation, is disclosed.

1 Drawing Sheet

Genus and species: *Calibrachoa* sp.
Variety denomination: 'KLECA20803'.

BACKGROUND OF THE NEW PLANT

The present invention comprises a new and distinct variety of *Calibrachoa*, botanically known as *Calibrachoa* sp., and hereinafter referred to by the variety name 'KLECA20803'. 'KLECA20803' originated from a controlled cross in August 2017 in Stuttgart, Germany between the proprietary female *Calibrachoa* parent 'CA-2013-0250' (unpatented) and the proprietary male *Calibrachoa* 'CA-2015-6388' (unpatented). Progeny from the cross were planted and a single plant was selected in May 2018 in Stuttgart, Germany.

'KLECA20803' has been found to reproduce true to type in successive generations of asexual propagation in Stuttgart, Germany via vegetative tip cuttings.

SUMMARY

The following are the most outstanding and distinguishing characteristics of 'KLECA20803' when grown under normal horticultural practices in Stuttgart, Germany and Latina, Italy.

1. A semi-trailing plant habit; and
2. Yellow flowers with red venation.

DESCRIPTION OF THE PHOTOGRAPH

This new *Calibrachoa* plant is illustrated by the accompanying photograph of a plant grown outdoors in Stuttgart, Germany. The photograph shows the whole plant, including the flowers and foliage and buds. The colors shown are as true as can be reasonably obtained by conventional photographic procedures. The photograph is of a plant that is 12-weeks-old, taken indoors in May 2019 in Stuttgart, Germany.

DESCRIPTION OF THE NEW VARIETY

The following detailed descriptions set forth the distinctive characteristics of 'KLECA20803'. The data which define these characteristics were collected from asexual reproductions carried out in Latina, Italy. Data was collected on plants grown 14-weeks since potting in a greenhouse with no pinching and using BONZI. Color references are to The R.H.S. Colour Chart of The Royal Horticultural Society of London (R.H.S.), 5$^{th}$ edition (2007).

Classification:
- *Family*.—Solanaceae.
- *Botanical*.—*Calibrachoa* sp.
- *Designation*.—'KLECA20803'.

Parentage:
- *Female parent*.—'CA-2013-0250' (unpatented).
- *Male parent*.—'CA-2015-6388' (unpatented).

Plant:
- *Life cycle*.—Annual.
- *Form*.—Short-lived subshrub.
- *Habit*.—Semi-trailing.
- *Height (from soil line to top of foliage)*.—18.5 cm.
- *Spread*.—43.0 cm.
- *Propagation type*.—Vegetative tip cuttings.
- *Time to produce a rooted cutting*.—3 weeks.
- *Pests and disease resistance*.—No particular pest or disease resistance observed to date.

Stems:
- *Stem color*.—RHS 145A (Yellow-Green).
- *Pubescence*.—Present.
- *Pubescence color*.—RHS 155A (White).
- *Stem diameter*.—0.1 cm.
- *Stem length*.—From soil line to first node: 0.8 cm. Total length: 30.0 cm.
- *Internode length*.—3.8 cm.

Foliage:
- *Arrangement*.—Opposite.
- *Shape*.—Obtuse.
- *Apex*.—Obtuse.
- *Base*.—Obtuse.
- *Margin*.—Ciliate.
- *Variegation*.—Absent.

*Surface texture*.—Upper surface: Smooth. Lower surface: Pubescent.
*Pubescence color*.—RHS 155A (White).
*Venation*.—Pinnate.
*Venation color*.—Upper surface: RHS 144A (Yellow-Green). Lower surface: RHS 144A (Yellow-Green).
*Length*.—2.9 cm.
*Width*.—0.3 cm to 1.1 cm.
*Color*.—Upper surface: RHS 137C (Green). Lower surface: RHS 138B (Green).
*Fragrance*.—Absent.
*Petiole*.—Absent; sessile.

Inflorescence:
*Flowering type*.—Single flowers.
*Flowering requirements*.—A minimum of light sun is required.
*Flowering season*.—Continuous flowering from spring through autumn and all the time OR year around in a greenhouse environment.
*Duration of flowers*.—6 days.
*Corolla texture*.—Smooth.
*Shape*.—Funnel form.
*Lobing of the flower*.—Weak.
*Fragrance*.—Absent.
*Flowers per plant*.—About 40 to 50.
*Flower depth*.—3.0 cm.
*Flower diameter*.—3.6 cm.
*Flower tube length*.—1.6 cm.
*Flower tube diameter*.—0.5 cm.
*Flower throat diameter*.—0.8 cm.
*Pedicel color*.—RHS 144B (Yellow-Green).
*Pedicel length*.—1.8 cm.

Flower bud:
*Surface texture*.—Pubescent.
*Typical number of buds per plant at any time*.—About 30 to 40.
*Length*.—2.0 cm.
*Diameter*.—0.4 cm.
*Shape*.—Irregular to oblong.
*Color*.—RHS 150C (Yellow-Green).

Peduncles:
*Length*.—1.9 cm to 3.5 cm.
*Diameter*.—0.1 cm.
*Color*.—RHS 144B (Yellow-Green).
*Texture*.—Pubescent.
*Anthocyanin color*.—Absent.

Sepals:
*Calyx*.—Funnel-shaped, salver-form.
*Shape*.—Obtuse.
*Surface texture* (*both upper and lower surfaces*).—Pubescent.
*Quantity per flower*.—5.
*Apex*.—Obtuse.
*Base*.—Fused.
*Margin*.—Ciliate.
*Length*.—1.1 cm.
*Diameter*.—0.35 cm.
*Sepal color*.—Upper surface: RHS 138A (Green). Lower surface: RHS 138B (Green).

Petals:
*Shape*.—Obcordate.
*Quantity per flower*.—5 fused petals, each petal comprised of 2 lobes.
*Length* (*without tube*).—1.4 cm.
*Apex*.—Truncate.
*Margin*.—Entire.
*Base*.—Fused into the tube.
*Texture*.—Upper surface: Smooth. Lower surface: Smooth.
*Lobe length*.—1.4 cm.
*Lobe width*.—1.8 cm.
*Color*.—Lobe color: Upper surface: RHS 4A (Yellow) and fading to RHS 4B (Yellow); transition lobe color is RHS 46B (Red) and fading to RHS 50B (Red) and transition size is small and rounded; venation color is RHS 46B (Red) and fading to RHS 50B (Red). Lower surface: RHS 2C (Yellow) and fading to RHS 2D (Yellow); transition lobe color is RHS N57B (Red-Purple) and fading to RHS N57D (Red-Purple); venation color is RHS 165A (Greyed-Orange) and fading to RHS N144A (Yellow-Green). Corolla tube color: Inner surface: RHS 1B (Yellow). Outer: RHS 154C (Yellow-Green) with RHS 138B (Green) veins.
*Fragrance*.—Absent.

Reproductive organs:
*Stamen number*.—5.
*Anther color*.—RHS 8A (Yellow).
*Anther shape*.—Bi-lobed and ovoid.
*Anther length*.—Less than 0.1 cm.
*Filament color*.—RHS 154D (Yellow-Green).
*Filament length*.—0.5 cm.
*Pollen color*.—RHS 6A (Yellow).
*Pollen amount*.—Abundant.
*Placenta arrangement*.—Basal.
*Pistil number*.—1.
*Pistil length*.—0.8 cm.
*Stigma color*.—RHS 145B (Yellow-Green).
*Stigma shape*.—Rounded.
*Style length*.—0.7 cm.
*Style color*.—RHS 145C (Yellow-Green).

Fruit and seed set: No fruit or seed set observed.

COMPARISON OF 'KLECA20803' WITH PARENTAL LINES AND KNOWN VARIETY

'KLECA20803' is a distinct variety of *Calibrachoa* and is distinguished from its parents as described in Table 1.

TABLE 1

Comparison with Parental Lines

| Characteristic | 'KLECA20803' | Female Parent 'CA-2013-0250' | Male Parent 'CA-2015-6388' |
|---|---|---|---|
| Earliness to flower | Flowers earlier than each parent | Medium - flowers 2 days later than 'KLECA20803' | Medium - flowers 2 days later than 'KLECA20803' |

'KLECA20803' is a distinct variety of *Calibrachoa* and differences between 'KLECA17003' (unpatented), also known as MINIFAMOUS 'Uno Yellow' are described in Table 2.

TABLE 2

| Comparison with Similar Variety | | |
|---|---|---|
| Characteristic | 'KLECA20803' | 'KLECA17003' |
| Earliness to flower | Flowers 2 days earlier than 'KLECA17003' | Flowers 2 days later than 'KLECA20803' |

TABLE 2-continued

| Comparison with Similar Variety | | |
|---|---|---|
| Characteristic | 'KLECA20803' | 'KLECA17003' |
| Growth habit | More compact than 'KLECA17003' | Less compact than 'KLECA20803' |

I claim:

1. A new and distinct variety of *Calibrachoa* plant designated 'KLECA20803' as illustrated and described herein.

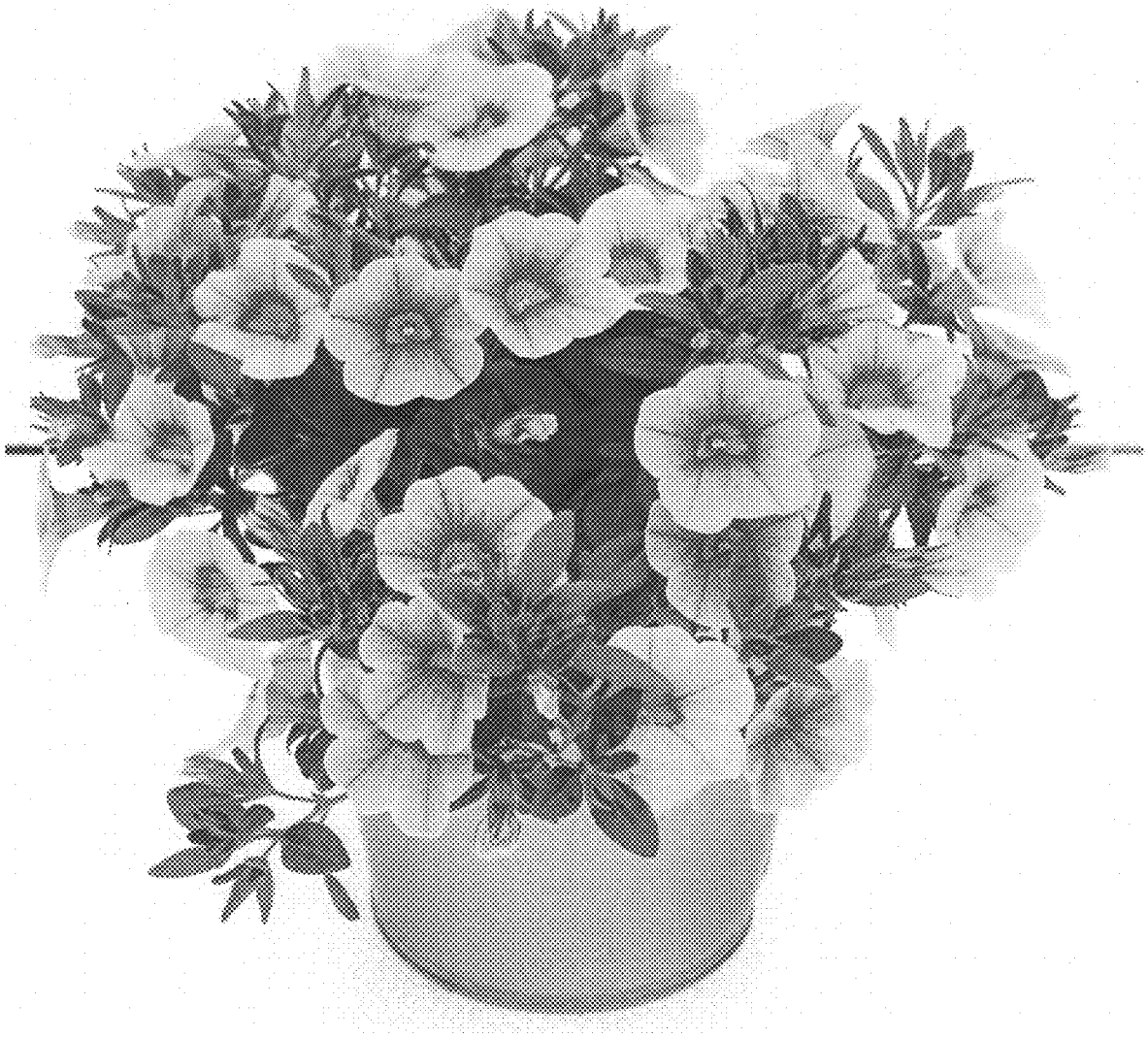

* * * * *